US008426148B2

(12) United States Patent
Fang et al.

(10) Patent No.: US 8,426,148 B2
(45) Date of Patent: *Apr. 23, 2013

(54) LABEL-FREE METHODS USING A RESONANT WAVEGUIDE GRATING BIOSENSOR TO DETERMINE GPCR SIGNALING PATHWAYS

(75) Inventors: Ye Fang, Painted Post, NY (US); Y. Alice Gao, Corning, NY (US); Elizabeth Tran, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 1196 days.

This patent is subject to a terminal disclaimer.

(21) Appl. No.: 11/998,711

(22) Filed: Nov. 30, 2007

(65) Prior Publication Data

US 2012/0135423 A1    May 31, 2012

Related U.S. Application Data

(60) Provisional application No. 60/997,910, filed on Oct. 6, 2007.

(51) Int. Cl.
*G01N 33/567* (2006.01)
*G01N 33/53* (2006.01)

(52) U.S. Cl.
USPC .......................... 435/7.21; 435/7.2

(58) Field of Classification Search .................. None
See application file for complete search history.

(56) References Cited

U.S. PATENT DOCUMENTS

| | | | | |
|---|---|---|---|---|
| 4,815,843 A | 3/1989 | Tiefenthaler et al. | ......... | 356/128 |
| 5,305,074 A | 4/1994 | Feldman | ................. | 356/345 |
| 5,738,825 A | 4/1998 | Rudigier et al. | ............ | 422/82.11 |
| 5,830,766 A | 11/1998 | Attridge et al. | ................ | 436/518 |
| 6,233,471 B1 | 5/2001 | Berner et al. | ................. | 600/345 |
| 6,340,598 B1 | 1/2002 | Herron et al. | ................. | 436/518 |
| 6,707,561 B1 | 3/2004 | Budach et al. | ................. | 356/521 |
| 6,727,071 B1 | 4/2004 | Dunlay et al. | ................. | 435/7.21 |
| 6,818,886 B2 | 11/2004 | Tiefenthaler | ................ | 250/282 |
| 6,867,869 B2 | 3/2005 | Budach et al. | ................. | 356/521 |
| 6,870,630 B2 | 3/2005 | Budach et al. | ................. | 356/521 |
| 6,893,705 B2 | 5/2005 | Thomas et al. | ................. | 428/141 |
| 6,985,664 B2 | 1/2006 | Caracci et al. | ................. | 385/130 |
| 7,064,844 B2 | 6/2006 | Budach et al. | ................. | 356/521 |
| 7,105,347 B2 | 9/2006 | Fang et al. | ..................... | 435/455 |
| 7,264,973 B2 | 9/2007 | Lin et al. | ........................ | 436/518 |
| 7,286,221 B2 | 10/2007 | Caracci et al. | ................. | 356/300 |
| 7,627,201 B2 | 12/2009 | Tiefenthaler | .................... | 385/12 |
| 2002/0127565 A1 | 9/2002 | Cunningham et al. | ............ | 435/6 |
| 2002/0160534 A1 | 10/2002 | Herron et al. | ................. | 436/518 |
| 2002/0164824 A1 | 11/2002 | Xiao et al. | ..................... | 436/524 |
| 2002/0168295 A1 | 11/2002 | Cunningham et al. | ...... | 422/82.05 |
| 2003/0012692 A1 | 1/2003 | Lemee et al. | .................... | 422/57 |
| 2003/0017580 A1 | 1/2003 | Cunningham et al. | ..... | 435/287.2 |
| 2003/0017581 A1 | 1/2003 | Li et al. | ....................... | 435/287.2 |
| 2003/0026891 A1 | 2/2003 | Qiu et al. | ........................ | 427/58 |
| 2003/0027327 A1 | 2/2003 | Cunningham et al. | ..... | 435/287.2 |
| 2003/0027328 A1 | 2/2003 | Cunningham et al. | ..... | 435/287.2 |
| 2003/0032039 A1 | 2/2003 | Cunningham et al. | ............ | 435/6 |
| 2003/0059855 A1 | 3/2003 | Cunningham et al. | ......... | 435/7.9 |
| 2003/0068657 A1 | 4/2003 | Lin et al. | ......................... | 435/7.9 |
| 2003/0077660 A1 | 4/2003 | Pien et al. | ...................... | 435/7.1 |
| 2003/0092075 A1 | 5/2003 | Pepper | .............................. | 435/7.9 |
| 2003/0113766 A1 | 6/2003 | Pepper et al. | ...................... | 435/6 |
| 2003/0124516 A1 | 7/2003 | Chung et al. | ...................... | 435/5 |
| 2003/0138208 A1 | 7/2003 | Pawlak et al. | .................... | 385/37 |
| 2003/0194755 A1 | 10/2003 | Schnabel et al. | ............. | 435/7.23 |
| 2003/0211461 A1 | 11/2003 | Kariv et al. | ....................... | 435/4 |
| 2004/0009540 A1 | 1/2004 | Soohoo et al. | ................ | 435/7.23 |
| 2004/0023310 A1 | 2/2004 | Kariv et al. | ...................... | 435/7.2 |
| 2004/0033539 A1 | 2/2004 | Schnabel et al. | ............. | 435/7.21 |
| 2004/0053209 A1 | 3/2004 | Kariv et al. | ........................ | 435/4 |
| 2004/0091397 A1 | 5/2004 | Picard | ............................ | 422/99 |
| 2004/0132172 A1 | 7/2004 | Cunningham et al. | ..... | 435/287.2 |
| 2004/0151626 A1 | 8/2004 | Cunningham et al. | ............ | 422/58 |
| 2004/0223881 A1 | 11/2004 | Cunningham et al. | ..... | 422/82.05 |
| 2004/0235198 A1 | 11/2004 | Marx et al. | ..................... | 436/527 |
| 2004/0263841 A1 | 12/2004 | Caracci et al. | ................ | 356/300 |
| 2005/0070027 A1 | 3/2005 | Gollier et al. | ................. | 436/518 |
| 2005/0100904 A1 | 5/2005 | Yoshizato et al. | ................ | 435/6 |
| 2005/0158880 A1 | 7/2005 | Ostuni et al. | ...................... | 438/1 |
| 2005/0236554 A1 | 10/2005 | Fontaine et al. | ............ | 250/208.1 |
| 2006/0063276 A1 | 3/2006 | Jiang et al. | ..................... | 436/518 |
| 2006/0205058 A1 | 9/2006 | Frutos et al. | ............... | 435/287.1 |
| 2006/0205092 A1 | 9/2006 | Lackritz et al. | ............... | 436/525 |
| 2006/0223051 A1 | 10/2006 | Fang et al. | ......................... | 435/4 |
| 2009/0142790 A1* | 6/2009 | Fang et al. | ...................... | 435/29 |

FOREIGN PATENT DOCUMENTS

| | | |
|---|---|---|
| WO | WO 01/57530 | 8/2001 |
| WO | WO 02/08762 | 1/2002 |
| WO | WO 2004/044171 | 5/2004 |
| WO | WO 2005/005979 | 1/2005 |

(Continued)

OTHER PUBLICATIONS

Conway BR and Demarest KTT, Receptors Channels 8(5-6):331-341, 2002.*
D.R. Alessi et al., "PD 098059 Is a Specific Inhibitor of the Activation of Mitogen-activated Protein Kinase Kinase in Vitro and in Vivo", *The Journal of Biological Chemistry*, Nov. 17, 1995, vol. 270, No. 46, pp. 27489-27494.
M. Azzi et al., "β-Arrestin-mediated activation of MAPK by inverse agonists reveals distinct active conformations for G Protein-coupled receptors", *PNAS*, Sep. 30, 2003, vol. 100, No. 20, pp. 11406-11411.
Z. Bajzer et al., "Binding, Internalization, and Intracellular Processing of Proteins Interacting with Recycling Receptors", *The Journal of Biological Chemistry*, Aug. 15, 1989, vol. 264, No. 23, pp. 13623-13631.

(Continued)

*Primary Examiner* — Robert Landsman
(74) *Attorney, Agent, or Firm* — John L. Haack

(57) ABSTRACT

A system and method for GPCR signaling pathway analysis and elucidation using a biosensor, a live-cell, and a pathway active compound, as defined herein.

20 Claims, 7 Drawing Sheets

FOREIGN PATENT DOCUMENTS

| WO | WO 2005/017507 | 2/2005 |
| WO | WO 2006/107967 | 10/2006 |
| WO | WO 2006/108183 | 10/2006 |
| WO | WO 2007/018872 | 2/2007 |

OTHER PUBLICATIONS

J.G. Baker et al., "Influence of Agonist Efficacy and Receptor Phosphorylation on Antagonsit Affinity Measurements: Differences between Second Messenger and Reporter Gene Responses", *Mol. Pharmacol.*, 2003; vol. 64, No. 3, pp. 679-688.

D.W. Barnes, "Epidermal Growth Factor Inhibits Growth of A431 Human Epidermoid Carcinoma in Serum-free Cell Culture", *The Journal of Cell Biology*, Apr. 1982, vol. 93, pp. 1-4.

O. Beske at al., "A Novel Encoded Particle Technology that Enables Simultaneous Interrogation of Multiple Cell Types", *The Society of Biomolecular Screening*, 2004, vol. 9, No. 3, pp. 173-185.

Brecht et al ; "Optical Probes and Transducers", *Biosensors and Bioelectrortics*, vol. 10, 1995, pp. 923-936.

W. Budach et al., "Planar Waveguides as High-Performance Sensing Platforms for Fluorescence-Based Multiplexed Oligonucleotide Hybridization Assays", *Anal Chem.*, 1999, vol. 71, pp. 3347-3355.

P. Burke et al., "Regulation of Epidermal Growth Factor Receptor Signaling by Endocytosis and Intracellular Trafficking", *Molecular Biology of the Cell*, Jun. 2001, vol. 12, pp. 1897-1910.

K. Choudhuri et al., "T-cell receptor triggering is critically dependent on the dimensions of its peptide-MHC ligand", *Nature*, vol. 436, Jul. 28, 2005, pp. 578-582.

Clerc et al., "Direct Immunosensing With an Integrated-Optical Output Grating Coupler"; *Sensors & Actuators B*, vol. 40, 1997, pp. 53-58.

B. Cunningham et al., "Label-Free Assays on the BIND System", *The Society for Biomolecular Screening*, 2004, vol. 9, No. 6, pp. 481-490.

Y. Danjo et al., "Actin "purse string" filaments are anchored by E-cadherin-mediated adherens junctions at the leading edge of the epithelial wound, providing coordinated cell movement", *Journal of Cell Science*, 1998, vol. 111, pp. 3323-3331.

R.J. Daly, "Take Your Partners, Please—Signal Diversification by the erbB Family of Receptor Tyrosine Kinases", *Growth Factors*, vol. 16, pp. 255-263, (1999).

H. Daub et al., "Role of transactivation of the EGF receptor in signalling by G-protein-coupled receptors", *Nature*, Feb. 8, 1996, vol. 379, pp. 557-560.

Drews, "Drug Discovery: A Historical Perspective", *Science*, Mar. 17, 2000, vol. 287, pp. 1960-1964.

G.L. Duveneck et al., "Novel Bioaffinity Sensors for Trace Analysis Based on Luminescence Excitation by planar Waveguides", *Sensors and Actuators B*, vol. 38-39, 1997, pp. 88-95.

G.L. Duveneck et al., "Review on Fluorescence-Based Planar Waveguide Biosensors", *Proc. SPIE*, vol. 3858, 1999, pp. 59-71.

G.L. Duveneck et al., "Two-Photon Fluorescence Excitation of Macroscopic Areas on Planar Waveguides", *Biosensors and Bioelectronics*, vol. 18, 2003, pp. 503-510.

P.L. Edmiston et al., "Dipole Orientation Distributions in Langmuir—Blodgett Films by Planar Waveguide Linear Dichroism and Fluorescence Anisotropy", *J. Phys. Chem.*, 1996, vol. 100, pp. 775-784.

Ye Fang et al., "Cellular functions of cholesterol probed with optical biosensors", *Biochimica et Biophysica Acta*, vol. 1763, 2006, pp. 254-261.

Y. Fang et al., "Characteristics of Dynamic Mass Redistribution of Epidermal Growth. Factor Receptor Signaling in Living Cells Measured with Label-Optical Biosensors", *Anal. Chem.*, vol. 77, 2005, pp. 5720-5725.

Y. Fang et al., "G-Protein-Coupled Receptor Microarnlys", *ChemBioChem*, Oct. 4, 2002, vol. 3, No. 10, pp. 987-991.

Y. Fang, "Label-Free Cell-Based Assays with Optical Biosensors in Drug Discovery", *Assay and Drug Development Technologies*, vol. 4, No. 5, 2006, pp. 583-595.

Y. Fang et al., "Non-Invasive Optical Biosensor for Assaying: Endogenous G Protein-Coupled Receptors in Adherent Cells", *Journal of Pharmacological and Toxicological Method*, vol. 55, 2001, pp. 314-322.

Y. Fang et al., "Optical biosensor differentiates signalling of endogenous $PAR_1$ and $PAR_2$ in A431 cells", *BMC Cell Biology*, 2007, vol. 8, No. 24, pp. 1-12, http://www.biomedcentral.com/1471-2121/8/24.

Ye Fang et al., "Optical Biosensor provides Insights for Bradykinin B2 Receptor Signaling in A431 Cells", *FEBS Letters*, vol. 579; 2005; pp. 6365-6374.

Y. Fang et al., "Probing cytoskeleton modulation by optical biosensors", *FEBS Letters*, vol. 579, 2005, pp. 4175-4180.

Y. Fang et al., "Resonant Waveguide Grating Biosensor for Living Cell Sensing", *Biophysical Journal*, vol. 91, Sep. 2006, pp. 1925-1940.

A.R. French et al., "Postendocytic Trafficking of Epidermal Growth Factor-Receptor Complexes Is Mediated Through Saturable and Specific Endosomal Interactions", *The Journal of Biological Chemistry*, Jun. 3, 1994, vol. 269, No. 22, pp. 15749-15755.

I. Giaever et al., "Monitoring fibroblast behaviour in tissue culture with an applied electric field", *Proc. Natl. Acad. Sci.*, Jun. 1984, vol. 81, pp. 3761-3764.

A. Glading et al., "Epidermal Growth Factor Receptor Activation of Calpain Is Required for Fibroblast Motility and Occurs via an ERK/MAP Kinase Signaling Pathway", *The Journal of Biological Chemistry*, Jan. 28, 2000, vol. 275, No. 4, pp. 2390-2398.

H.M. Grandin et al., "Waveguide Excitation ,Fluorescence Microscopy: A New Tool for Sensing and Imaging the Biointerface", *Biosensors and Bioelectronics*, vol. 21, 2006, pp. 1476-1482.

A. Graness et al., "Protein-tyrosine-phosphatase-mediated epidermal growth factor (EGF) receptor transinactivation and EGF receptor-independent stimulation of mitogen-activated protein kinase by bradykinin in A431 cells", *Biochem. J.*, 2000, vol. 347, pp. 441-447.

A. Grakoui et al., "The Immunological Synapse: A Molecular Machine Controlling T Cell Activation", *Science*, vol. 285, Jul. 9, 1999, pp. 221-227.

S.A. Green et al., "Sustained Activation of a G Protein-coupled Receptor via "Anchored", Agonist Binding", *The Journal of Biological Chemistry*, vol. 271; No. 39, pp. 24029-24035, (1996).

A. Gschwind et al., "Cell communication networks: epidermal growth factor receptor transactivation as the paradigm for interrreceptor signal transmission", *Oncogene*, 2001, vol. 20, pp. 1594-1600.

M. Halter et al., "Enhanced Optical Waveguide Light Mode Spectroscopy Via Detection of Fluorophore Absorbance", *Review of Scientific Instruments*, vol. 77; 2006, pp. 103105-1-103106

M. Hide et al., "Real-Time Analysis of Ligand-Induced Cell Surface and Intracellular Reactions of Living Mast Cells Using a Surface Plasmon Resonance-Based Biosensor", *Analytical Biochemistry*, vol. 302, 2002, pp. 28-37.

W.R. Holland et al., "Waveguide Mode Enhancement of Molecular Fluorescence", *Optics Letters*, vol. 10, No. 8, Aug. 1985, pp. 414-416.

R. Horváth et al., "Effect of patterns and inhomogeneities on the surface of waveguides used for optical waveguide lightmode spectroscopy applications", *Applied Physics B*, 2001, vol. 72, pp. 441-447.

R. Horváth et al., "Reverse-symmetry waveguides: theory and fabrication", *Applied Physics B*, 2002, vol. 74, pp. 383-393.

Y. Huang et al., "Growth Hormone-induced Phosphorylation of Epidermal Growth Factor (EGF) Receptor in 3T3-F442A Cells", *The Journal of Biological Chemistry*, May 23, 2003, vol. 278, No. 21, pp. 18902-18913.

W. Huber et al., "Direct optical immunosensing (sensitivity and selectivity)", *Sensors and Actuators B*, 1992, vol. 6, pp. 122-126.

B. January et al.,"$β_2$-Adrenergic Receptor Desensitization, Internationalization, and Phosphorylation in Response to Full and Partial Agonists", *The Journal of Biological Chemistry*, vol. 272, No. 38, pp. 23871-23879, (1997).

Jin et al., "A Biosensor Concept Based on Imaging Ellipsometiy for Visualization of Biomolecular Interactions", *Analytical Biochemistry*, vol. 232, 1995, pp. 69-72.

C.E. Jordan et al., "Surface Plasmon Resonance Imaging Measurements of DNA Hybridization Adsorption and Streptavidin/DNA Multilayer Formation at Chemically Modified Gold Surfaces", *Anal. Chem.*, 1997, pp. 4939-4947.

Jordan et al., "Surface Plasmon Resonance Imaging Measurements of Electrostatic Biopolymer Adsorption Onto Chemically Modified Gold Surfaces", *Anal. Chem.*, 1997, vol. 69, pp. 1449-1456.

P. Lalanne et al., "Highly Improved Convergence of the Coupled-Wave Method for TM Polarization", *J. Opt. Soc. Am. A*, vol. 13, No. 4; Apr. 1996, pp. 779-784.

M.A. Lemmon et al., "Regulation of signal transduction and signal diversity by receptor oligomerization", *Trends Biochem. Sci.*, 1994, vol. 19, pp. 459-463.

G. Liapakis et al., "Synergistic Contributions of the Functional Groups of Epinephrine to its Affinity and Efficacy at the $\beta_2$ Adrenergic Receptor", *Mol. Pharmacol.*, 2004, vol. 65, No. 5, pp. 1181-1190.

G. Liapakis et al., "The Forgotten Serine", *The Journal of Biological Chemistry*, vol. 275, No. 48, pp. 37779-37788, (2000).

Y. Liu et al., "Structural basis for selective inhibition of Src family kinases by PP1 ", *Chemistry & Biology6*, 1999, vol. 6, No. 9, pp. 671-678.

E. Livneh et al., "Reconstitution of Human Epidermal Growth Factor Receptors and its Deletion Mutants in Cultured Hamster Cells", *The Journal of Biological Chemistry*, Sep. 25, 1986, vol. 261, No. 27, pp. 12490-12497.

L. Lorenzelli, et al., "Bioelectrochemical signal monitoring of in-vitro cultured cells by means of an automated microsystem based on solid state sensor-array", *Biosensors and Bioelectronics*, 2003, vol. 18, pp. 621-626.

Z. Lu et al., "Epidennal Growth Factor-Induced Tumor Cell Invasion and Metastasis Initiated by Dephosphorylation and Downregulation of Focal Adhesion Kinase", *Molecular and Cellular Biology*, Jun. 2001, vol. 21, No. 12, pp. 4016-4031.

Ma et al., "From the Analyst's Couch: Value of Novelty?", *Nature Reviews, Drug Discovery*, vol. 1, Aug. 2002, pp. 571-572.

Morhard et al., "Immobilization of Antibodies in Micropatterns for Cell Detection by Optical Diffraction", *Sensors and Actuators B*, vol. 70, 2000, pp. 232-242.

K. Mossman et al., "Micropattenied supported membranes as tools for quantitative studies of the immunological synapse", *Chemical Society Reviews*, vol. 36, 2007, pp. 46-54.

B.S. Negrutskii et al., "A sequestered pool of aminoacyl-tRNA in mammalian cells", *Proc. Natl. Acad. Sci. USA*, 1992, vol. 89, pp. 3601-3604.

B.S. Negrutskii et al., "Supramolecular organization of the mammalian translation system", *Proc. Natl. Acari Sci. USA*, 1994, vol. 91, pp. 964-968.

P.M. Nellen et al., "Integrated Optical Input Grating Couplers as Biochemical Sensors", *Sensors and Actuators*, 1988, vol. 15, pp. 285-295.

Y. Nong et al., "Glycine binding primes NMDA receptor internalization", *Nature*, Mar. 20, 2003, vol. 422, pp. 302-307.

Pierce et al., "Seven-Transmembrane Receptors", *Nature Reviews, Molecular Cell Biology*, vol. 3, Sep. 2002, pp. 639-650.

G. Powis et al., "Wortmannin, a Potent and Selective Inhibitor of Phosphatidylinositol-3-kinase[1]", *Cancer Research*, May 1, 1994, vol. 54, pp. 2419-2423.

Ramsden et al., "Kinetics of Adhesion and Spreading of Aninial Cells", *Biotechnology and Bioengineering*, vol. 43, 1994, pp. 939-945.

H. Resat et al., "An Integrated Model of Epidermal Growth Factor Receptor Trafficking and Signal Transduction", *Biophysical Journal*, Aug. 2003, vol. 85, pp. 730-743.

C. Rosette et al., "Ultraviolet Light and Osmotic Stress: Activation of the JNK Cascade Through Multiple Growth Factor and Cytokine Receptors", *Science*, Nov. 15, 1996, vol. 274, pp. 1194-1197.

M.D. Salik et al., Resonant Excitation Analysis of Waveguide Grating Couplers, *Optics Communications*, vol. 193, Jun. 15, 2001, pp. 127-131.

J. Schlessinger, "Cell Signaling by Receptor Tyrosine Kinases", *Cell*, Oct. 13, 2000, vol. 103, pp. 211-225.

B. Schoeber et al., "Computational modelling of the dynamics of the MAP kinase cascade activated by surface and internalized EGF receptors", *Nature Biotechnology*, Apr. 2002, vol. 20, pp. 370-375.

M.A. Simmons, "Functional Selectivity, Ligand-Directed Trafficking, Conformation-Specific Agonism: What's in a Name?", *Molecular Interventions*, Jun. 2005, vol. 5, Issue 3, pp. 154-157.

E.A. Smith et al., "Surface Plasmon Resonance Imaging as a Tool to Monitor Biomolecular Interactions in an Array Based Format" *Applied Spectroscopy*, 2003, vol. 57, No. 11, pp. 320A-332A.

K. Solly et al., "Application of Real-Time Cell Electronic Sensing (RT-CES) Technology to Cell-Based Assays", *ASSAY and Drug Development Technologies*,2004, vol. 2, No. 4, pp. 363-372.

G. Swaminath et al., "Probing the $\beta_2$ Adrenoceptor Binding Site with Catechol Reveals Differences in Binding and Activation by Agonists and Partial Agonists", *The Journal of Biological Chemistry*, vol. 280, No. 23, pp. 22165-22171 (2005).

Tiefenthaler et al., "Intregrated Optical Switches and Gas Sensors", *Optics Letters*, Apr. 1984, vol. 10, No. 4, pp. 137-139.

K. Tiefenthaler et al., "Sensitivity of grating couplers as integrated-optical chemical sensors", *J. Opt. Soc. Am. B*, Feb. 1989, vol. 6, No. 2, pp. 209-220.

P.K. Tien, "Integrated optics and new wave phenomena in optical waveguides", *Reviews of Modern Physics*, Apr. 1977, vol. 49, No. 2, pp. 361-454.

J.D. Urban et al., "Functional Selectivity and Classical Concepts of Quantitative Pharmacology", *The Journal of Pharmacology and Experimental Therapeutics*, vol. 320, No. 1, pp. 1-13, (2007).

E. Verdonk et al., "Cellular Dielectric Spectroscopy: A Label-Free Comprehensive Platform for Functional Evaluation of Endogenous Receptors", *ASSAY and Drug Development Technologies*, 2006, vol. 4, No. 5, pp. 609-619 .

P.J. Verveer, et al., "Quantitative Imaging of Lateral ErbB1 Receptor Signal Propagation in the Plasma Membrane", *Science*, Nov. 24, 2000, vol. 290, pp. 1567-1570.

G. Voirin et al., "$Si_3N_4/SiO_2$/Si Waveguide Grating for Fluorescent Biosensors", *Proc. SPIE*, vol. 3620, 1999, pp. 109-116.

J. Vörös et al., "Feasibility study of an online toxicological sensor based on the optical waveguide technique", *Biosensor & Bioelectronics*, 2000, vol. 15, pp. 423-429.

J. Vörös et al., "Optical Grating Coupler Biosensors", *Biomaterials*, vol. 23, 2002, pp. 3699-3710.

Z.H. Wang et al., "A label-Free Multisensing Immunosensor Based on Imaging Ellipsometry", *Anal. Chem.*, 2003, vol. 75, pp. 6119-6123.

L.C. Waters et al., "Microchip Device for Cell Lysis, Multiplex PCR Amplification, and Electrophoretic Sizing", *Anal. Chem.*, 1998. vol. 70, pp. 158-162.

R. Wetzker et al., "Transactivation joins multiple tracks to the ERK/MAPK cascade", *Nature Reviews Molecular Cell Biology*, Aug. 2003, vol. 4, pp. 651-657.

A.D. Zechnich et al., "Possible Interactions With Terfenadine or Astemizole", *West J. Med.*, Apr. 1994, vol. 160, No. 4, pp. 321-325.

P.N. Zeller et al., "Single-Pad Scheme for Integrated Optical Fluorescence Sensing", *Biosensors & Bioelectronics*, vol. 15, 2000, pp. 591-595.

Hug, T. S., et al., "Optical waveguide lightmode spectroscopy as a new method to study adhesion of anchorage-dependent cells as an indicator of metabolic state", Biosensors & Bioelectronics 16 (2001), p. 865-874.

Li, S-Y., "Measurement of Adhesion and Spreading Kinetics of Baby Hamster Kidney and Hybridoma Cells Using an Integrated Optical Method", Biotechnol. Prog. 1994, 10, p. 520-524.

Ramsden, J. J., "Optical Method for Measurement of Number and Shape of Attached Cells in Real Time", Cytometry 19, 1995, p. 97-102.

Hug, T. S., "Optical Waveguide Lightmode Spectroscopy (OWLS) to Monitor Cell Proliferation Quantitatively", Biotechnology and Bioengineering, vol. 80, No. 2, Oct. 20, 2002, p. 213-221.

Horvath, R., "Optical waveguide sensor for on-line monitoring of bacteria", Optics Letters, Jul. 15, 2003, vol. 28, No. 14, p. 1233-1235.

Hug, T. S., "Biophysical Methods for Monitoring Cell-Substrate Interactions in Drug Discovery", Assay and Drug Development Technologies, vol. 1, No. 3, 2003, p. 479-488.

Horvath, R., "Monitoring of living cell attachment and spreading using reverse symmetry waveguide sensing", Applied Physics Letters 86, (2005), 071101-1-071101-3.

Corso, C. D., "An investigation of antibody immobilization methods employing organosilanes on planar ZnO surfaces for biosensor applications", Biosensors and Bioelectronics 24, (2008), p. 805-811.

Y. Fang et al., "Optical biosensor differentiates signaling of endogenous $PAR_1$ and $PAR_2$ in A431 cells", BMC Cell Biology, Jun. 22, 2007, vol. 8, No. 24, http://www.biomedcentral.com/1471-2121/8/24.

Y. Fang et al., "Resonant Waveguide Grating Biosensor for Living Cell Sensing", Biophysical Journal, Sep. 2006, vol. 91, pp. 1925-1940.

* cited by examiner

3A

3B

4A

4B

7A

7B

US 8,426,148 B2

LABEL-FREE METHODS USING A RESONANT WAVEGUIDE GRATING BIOSENSOR TO DETERMINE GPCR SIGNALING PATHWAYS

CLAIMING BENEFIT OF PRIOR FILED U.S. APPLICATION

This application claims the benefit of U.S. Provisional Application Ser. No. 60/997,910, filed Oct. 6, 2007. The content of this prior filed U.S. application and the entire disclosure of any publications, patents, and patent documents mentioned herein are incorporated by reference.

BACKGROUND

The disclosure relates to optical biosensors, such as resonant waveguide grating (RWG) biosensors or surface plasmon resonance (SPR) biosensors, and more specifically to methods for GPCR signaling pathway analysis using biosensor-based live-cell assays.

SUMMARY

The disclosure provides direct and indirect methods to G protein-coupled receptor (GPCR) or like receptor signaling pathway analysis and pathway elucidation using biosensor-based live-cell assays.

DETAILED DESCRIPTION

Figure 1:
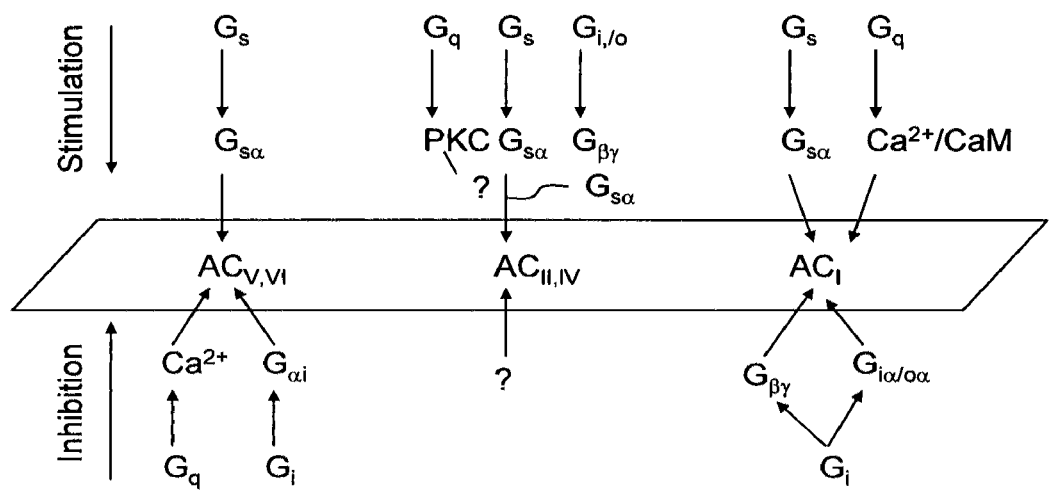
FIG. 1 is a schematic illustrating adenylate cyclase isoform-dependent cell signaling pathways, in embodiments of the disclosure.

Various embodiments of the disclosure will be described in detail with reference to drawings, if any. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Definitions

"Assay," "assaying" or like terms refers to an analysis to determine, for example, the presence, absence, quantity, extent, kinetics, dynamics, or type of a cell's optical or bio-impedance response upon stimulation with an exogenous stimuli, such as a ligand candidate compound, adenylate activator, cAMP analog, or a GPCR ligand or ligand candidate.

"Attach," "attachment," "adhere," "adhered," "adherent," "immobilized," or like terms generally refer to immobilizing, fixing, culturing, incubating, and like terms, for example, a cell, and like entities of the disclosure, to a surface, such as by physical absorption, chemical bonding, and like processes, or combinations thereof. Particularly, "cell attachment," "cell adhesion," or like terms refer to the interacting or binding of cells to a surface, such as by culturing, or interacting with cell anchoring materials, a compatibilizer (e.g., fibronectin, collagen, lamin, gelatin, polylysine, etc.), or both. In embodiments, immobilization of live-cells on a biosensor can include, for example, incubating live-cells on a biosensor surface to a confluency of from about 1 percent to about 99 percent biosensor surface coverage, and like confluency values, or ranges and values therein.

"Adherent cells" refers to a cell or a cell line or a cell system, such as a prokaryotic or eukaryotic cell, that remain(s) associated with, immobilized on, or in certain contact with the outer surface of a substrate. Such cells, after culturing, can withstand or survive washing and medium exchanging process, which is prerequisite to many cell-based assays. "Weakly adherent cells" refers to a cell or a cell line or a cell system, such as a prokaryotic or eukaryotic cell, which weakly interacts, or associates with or contacts the surface of a substrate during cell culture. However, these types of cells, for example, human embryonic kidney (HEK) cells, tend to dissociate easily from the surface of a substrate by physically disturbing approaches such as washing or medium exchange. "Suspension cells" refers to a cell or a cell line that is preferably cultured in a medium wherein the cells do not attach or adhere to the surface of a substrate during the culture. "Cell culture" or "cell culturing" refers to the process by which either prokaryotic or eukaryotic cells are grown under controlled conditions. "Cell culture" can refer to the culturing of cells derived from multicellular eukaryotes, especially animal cells, and to culturing of complex tissues and organs.

"Cell" or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems.

"Cell system" or like term refers to a collection of more than one type of cells or differentiated forms of a single type of cell, which interact with each other, thus performing a biological, physiological, or pathophysiological function. Such cell system includes, for example, an organ, a tissue, a stem cell, a differentiated hepatocyte cell, or like cells.

"Marker" or like term refers to a molecule, a biomolecule, or a biological that is able to modulate the activities of at least one cellular target (e.g., a $G_q$-coupled receptor, a $G_s$-coupled receptor, a $G_i$-coupled receptor, a $G_{12/13}$-coupled receptor, an ion channel, a receptor tyrosine kinase, a transporter, a sodium-proton exchanger, a nuclear receptor, a cellular kinase, a cellular protein, etc.), and can result in a reliably detectable output or response as measured by a biosensor. Depending on the class of the intended cellular target and its subsequent cellular event(s), a marker could be an activator, such as an agonist, a partial agonist, an inverse agonist, for example, for a GPCR or a receptor tyrosine kinase, an ion channel, a nuclear receptor, or a cellular enzyme adenylate cyclase. The marker could also be an inhibitor for certain classes of cellular targets, for example, an inhibitor or a disruptor for actin filament, or microtuble.

"Detect" or like terms refer to an ability of the apparatus and methods of the disclosure to discover or sense a sensed signaling pathway and to distinguish the sensed signaling pathway from an absence of pathway signaling.

"Identify" or like terms refer to an ability of the apparatus and methods of the disclosure to detect and elucidate a signaling pathway.

"Therapeutic candidate compound," "therapeutic candidate," "prophylactic candidate," "prophylactic agent," "ligand candidate," or like terms refer to a molecule or material, naturally occurring or synthetic, which is of interest for its potential to interact with a cell attached to the biosensor or a pathogen. A therapeutic or prophylactic candidate can include, for example, a chemical compound, a biological molecule, a peptide, a protein, a biological sample, a drug candidate small molecule, a drug candidate biologic molecule, a drug candidate small molecule-biologic conjugate, and like materials or molecular entity, or combinations thereof, which can specifically bind to or interact with at least one of a cellular target or a pathogen target such as a protein, DNA, RNA, an ion, a lipid, or like structure or component of a living cell or a pathogen.

"Biosensor" or a like term refers to a device for the detection of an analyte that combines a biological component with a physicochemical detector component. The biosensor typically consists of three parts: a biological component or element (such as tissue, microorganism, pathogen, cells, or combinations thereof), a detector element (operating in a physicochemical way such as optical, piezoelectric, electrochemical, thermometric, or magnetic), and a transducer associated with both components. The biological component or element can be, for example, a live-cell. In embodiments, an optical biosensor can comprise an optical transducer for converting a molecular recognition or molecular stimulation event in a living-cell into a quantifiable signal.

"Include," "includes," or like terms means including but not limited to.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. Whether modified by the term "about" the claims appended hereto include equivalents to these quantities.

"Consisting essentially of" in embodiments refers, for example, to a method for GPCR signaling pathway detection, analysis, or both as defined herein, a formulation, or a composition on the surface of the biosensor, and articles, devices, or apparatus of the disclosure, and can include the components or steps listed in the claims, plus other components or steps that do not materially affect the basic and novel properties of the compositions, articles, apparatus, and methods of making and use of the disclosure, such as particular reactants, particular additives or ingredients, a particular agent, a particular cell or cell line, a particular surface modifier or condition, a particular ligand candidate, or like structure, material, or process variable selected. Items that may materially affect the basic properties of the components or steps of the disclosure or may impart undesirable characteristics to the present disclosure include, for example, decreased affinity of the cell for the biosensor surface, anomalous or contrary cell activity in response to a ligand candidate or like stimulus, and like characteristics.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for components, ingredients, additives, cell types, pathogens, and like aspects, and ranges thereof, are for illustration only; they do not exclude other defined values or other values within defined ranges. The compositions, apparatus, and methods of the disclosure include those having any value or any combination of the values, specific values, more specific values, and preferred values described herein.

In embodiments the methods of the disclosure provide for an analysis, determination, or both, of the signaling pathway(s) of G protein-coupled receptors (GPCRs) by, for example, measuring the impact of forskolin-stimulated cells on the GPCR ligand-induced biosensor responses, and, for example, measuring the impact of GPCR ligand-stimulated cells on the forskolin-induced biosensor responses.

In embodiments the methods can include, for example, a method for GPCR signaling pathway determination, the method comprising:

immobilizing live-cells on a biosensor;

contacting the immobilized live-cells with a substance that elevates intracellular cAMP and activates protein kinase A in the live-cells;

contacting the substance contacted live-cells with a GPCR ligand; and detecting and comparing the GPCR ligand-induced biosensor response of the live-cells in the presence and absence of the substance.

In embodiments the methods can, for example, comprise:

incubating cells on a biosensor;

contacting the incubated cells with a substance that causes the elevation of intracellular cAMP level, and subsequently the activation of protein kinase A;

and contacting these adenylate activator or cAMP analog contacted cells with a GPCR ligand.

In embodiments the methods can include, for example, a method for GPCR signaling pathway determination, the method comprising:

immobilizing live-cells on a biosensor;

contacting the immobilized live-cells with a GPCR ligand;

contacting the GPCR ligand contacted live-cells with a substance that elevates intracellular cAMP and activates protein kinase A in the live-cells; and detecting and comparing the substance-induced biosensor response of the live-cells in the presence and absence of the GPCR ligand.

In embodiments the method can, for example, comprise:
incubating cells on a biosensor;
contacting the incubated cells with a substance that causes the elevation of intracellular cAMP level, and subsequently the activation of protein kinase A; and
contacting these adenylate activator or cAMP analog contacted cells with a GPCR ligand.

A substance that causes the elevation of intracellular cAMP level, and subsequent the activation of protein kinase A includes, for example, an adenylate activator, such as forskolin or its derivates, such as NKH477, 1,9-dideoxy-forskolin, 7-deacetyl-7-O-hemisuccinyl-forskolin; or a cell permeable cAMP analog, such as (S)-adenosine, cyclic 3',5'-(hydrogenphosphorothioate)triethyl ammonium, 8-bromoadenosine-3',5'-cyclic monophosphate (8-Br-cAMP), 8-chloroadenosine-3',5'-cyclic monophosphate, or N6,2'-O-dibutyryladenosine-3',5'-cyclic monophosphate. These cAMP analogs are cell membrane permeable, and can be directly taken up into the cells, and can directly cause the activation of cAMP-dependent protein kinase (protein kinase A, PICA).

In embodiments an alternative method can, for example, comprise:
incubating cells on a biosensor;
contacting the incubated cells with a GPCR ligand; and
contacting the GPCR ligand contacted cells with a substance that causes the elevation of intracellular cAMP level, and subsequent the activation of protein kinase A.

In embodiments an alternative method can include, for example, a method for GPCR signaling pathway determination, the method comprising:
immobilizing live-cells on a biosensor;
contacting the immobilized live-cells with a substance that suppresses intracellular phospholipase C (PLC) activity in the live-cells;
contacting the PLC suppressed live-cells with a GPCR ligand; and
detecting and comparing the GPCR ligand-induced biosensor response of the live-cells in the presence and absence of the substance.

In embodiments the method can, for example, comprise:
incubating cells on a biosensor;
contacting the incubated cells with a phospholipase C depressor or suppressor, such as U73122 or an interference RNA; and
contacting these phospholipase C suppressed cells with a GPCR ligand.

The disclosed methods can be useful in specifying, for example, the positive and negative impacts of a known therapeutic compound or an unknown therapeutic candidate compound on a GPCR signaling pathway. Thus, the above-mentioned methods can include a further step of pretreatment, intermediate treatment, or post-treatment of the incubated cells with a stimulus.

In embodiments the disclosure provides a method to de-convolute and elucidate the details of biochemical signaling pathways observed in a ligand-induced biosensor signal studies. The disclosed methods are applicable to all classes of GPCR signaling. The disclosed methods can differentiate different classes of G protein signaling, and can also differentiate signaling of GPCRs from signaling of non-GPCRs. The disclosed methods can use an adenylate cyclase (AC) activator (e.g., forskolin, NKH 447), independently, or in combination with a phospholipase C suppressor (e.g., U73122, a synthetic aminosteroid, i.e., 1-[6-[[17β-3-methoxyestra-1,3,5(10)-trien-17-yl]amino]hexyl]-1H-pyrrole-2,5-dione; or an interference RNA), as a tool for pathway analysis or de-convolution using a biosensor-based live-cell assay as described herein.

The disclosure provides a universal approach to deconvolute or elucidate signaling pathways using biosensor-based cell assays. In embodiments, the disclosed methods can involve a two-step assay. The disclosed methods can also provide useful information regarding cell signaling mediated through a receptor.

In embodiments, the disclosure provides methods to analyze the signaling pathways of G protein-coupled receptors (GPCRs) using label-free biosensor-based cell assays. The present methods are applicable to all classes of GPCR signaling in live-cells. The methods are based, in embodiments, on the impact of cAMP-elevated cells, phospholipase C-suppressed cells, or both, on GPCR ligand-induced biosensor responses, and on the impact of GPCR ligand-stimulated cells on cAMP producing chemical or cell permeable cAMP analog-induced biosensor responses. The biosensors that can be used include, for example, optical biosensors, such as surface plasmon resonance and resonant waveguide grating (RWG) biosensors, electrical biosensors such as bioimpedance biosensors, resonant mirrors, and like devices.

G protein-coupled receptors (GPCRs) are the largest family of cell surface receptors that share a common structural motif of seven α-helical transmembrane spanning domains joined by intra- and extra-cellular loops. GPCRs are expressed in virtually all tissues, with distinct expression patterns in different cell systems. The extracellular ligands for GPCRs are diverse, including biogenic amines, amino acids, ions, small peptides, proteins, and bioactive lipids. This diversity of GPCR activators underscores the physiological importance of this receptor class; more specifically, GPCRs control a wide variety of physiological processes including neurotransmission, chemotaxis, inflammation, cell proliferation, and like processes. GPCRs have been implicated in almost every major disease class including, for example, asthma, cancer, inflammation, and cardiovascular diseases.

Given their role in health and disease, and their potential for therapeutic intervention by small molecule drugs, GPCRs represent the largest and most successful class of drug-able targets in the human genome. About 50% of all clinically available drugs are active, directly or indirectly, on GPCRs, yet these drugs are active only on small percentages of all known GPCRs. It has been estimated that the human genome encodes for as many as 1,000 GPCRs, of which about 400 are non-chemosensory receptors, predicted to bind endogenous ligands. Many of these (about 150) are classified as "orphan" GPCRs for which their cognate ligands or biological functions are as yet unknown. "De-orphanization" (i.e., adoption or a determination of their cognate ligands or biological functions) of these receptors may provide new therapeutic targets and new therapies.

Continued success in GPCR drug discovery and development has seen an evolution in assay technologies and methodologies. Assays for GPCR screening can be broadly classified into whole-cell assays and cell-free assays. Cell-based assays provide a highly accurate representation of cellular behavior in response to stimulation. Compared to the data obtained using cell-free assays, direct measurements of the compound-modulated GPCR functions in cell systems offer far more useful information, such as the action, mode, and mechanisms of compounds under conditions more closely resembling the physiological environment. These benefits have promoted increased use of whole-cell systems for drug screening and testing.

GPCRs participate in a wide array of cell signaling pathways, mediated through both G protein-dependent and G protein-independent pathways, often in a ligand-dependent manner. GPCR signaling is encoded by the spatial and temporal flux of downstream signaling networks, which are tightly controlled by intracellular signaling and regulatory machineries. The consensus models describing GPCR signaling assume a receptor to be a functional monomeric entity interacting through its specific intracellular domains with a single G protein, once stabilized in its active conformation(s) by agonist binding. The binding of a ligand to a GPCR results, for example, in changes in the conformation of the receptor. The receptor activation may in turn lead to the activation of an associated G protein heterotrimer through the GTP-GDP exchange on $G_\alpha$ subunit. The activated G protein then modulates the activity of several intracellular enzymes, which in turn control the production of several key intracellular second messengers such as cyclic AMP (cAMP), cGMP, $Ca^{2+}$, inositol triphosphate, and arachidonic acid. These second messengers then act on several downstream targets including ion channels and kinases that regulate gene transcription and cell functions.

Because of the unpredictability in the intracellular signaling mediated by synthetic compounds, a single compound could behave as an agonist or antagonist, depending on the signaling events measured. Further, the lack of efficacy on a given event measured does not guarantee a lack of receptor activation. Thus, a rational GPCR screen should not rely on a single assay; rather, an integrated approach should be employed to measure a multitude of signaling events. Technologies that are independent of cell signaling pathway(s) should be superior to those pathway-biased assay technologies, given the recent findings that GPCR activation can also lead to G protein-independent signaling under many circumstances.

Biosensor-based cell assays allow one to monitor activation of endogenous receptors in a more physiologically relevant environment. Such non-invasive capability can provide a more attractive representation of ligand pharmacology. Most GPCR cell assays utilize certain engineering or manipulations of cells in order to achieve the desired sensitivity for robust and reliable detection. In these artificial systems, the potency or efficacy of a ligand might be altered due to, for example, the high expression level of the receptor or the interference of certain manipulations (e.g., GFP-tagging, or the act of transfection) on the cellular physiology of the targets. For example, $\alpha_{2A}$-adrenergic receptor ($\alpha_{2A}AR$) is commonly believed to couple to $G_{\alpha i}$ proteins, leading to the inhibition of adenylate cyclase activity. In native HEL 92.1.7 cells, the drug Levomed is an inverse agonist of $\alpha_{2A}AR$, causing an increase in cAMP production. However, in transfected PC10 fibroblasts Levomed was found to be a positive agonist, causing an inhibition of cAMP production.

In addition, biosensor-based cell assays bypass the need of fluorescent labels, which fluorescent labels are otherwise widely used for detection in many conventional assays. Such label independence can significantly improve the data quality of GPCR screens, since the interference of cell components, labels, or compounds having fluorescence is minimized or eliminated.

Biosensor-based cell assays measure integrated cellular responses. For example, a RWG biosensor monitors ligand-induced dynamic mass redistribution (DMR) in living cells, whereas an electrical biosensor measures ligand-induced bio-impedance changes in living cells. A ligand might activate more than one receptor in cells, and a receptor may lead to multiple signaling pathways. Because of this confounding potential, it can be very difficult to assign a specific pathway being activated to a ligand-induced biosensor response measured solely on the shape and dynamics of the biosensor response.

1. Biosensor-Based Cell Assays and Biosensor Substrate

Label-free cell-based assays generally employ a biosensor to monitor ligand-induced responses in living cells. A biosensor typically utilizes a transducer such as an optical, electrical, calorimetric, acoustic, or magnetic transducer, to convert a molecular recognition event or a ligand-induced change in a cell layer into a quantifiable signal. These label-free biosensors are commonly used for molecular interaction analysis, which involves characterizing how molecular complexes form and disassociate over time. Although the present invention is applicable to almost all types of biosensor surfaces, only RWG biosensor and electrical biosensors have been demonstrated.

RWG biosensors—An RWG biosensor consists of, for example, a substrate (e.g., glass), a waveguide thin film with an embedded grating structure, and a cell layer. The RWG biosensor utilizes the resonant coupling of light into a waveguide by way of a diffraction grating, leading to total internal reflection at the solution-surface interface, which in turn creates an electromagnetic field at the interface. This electromagnetic field is evanescent in nature, such that it decays exponentially from the sensor surface; the distance at which it decays to 1/e of its initial value is known as the penetration depth and is a function of the design of a particular RWG biosensor, but is typically on the order of about 200 nm. This type of biosensor exploits such evanescent waves to characterize ligand-induced alterations of a cell layer at or near the sensor surface.

Electrical biosensors—Electrical biosensors consist of, for example, a substrate (e.g., plastic), an electrode, and a cell layer. In this electrical detection method, cells are cultured on small gold electrodes arrayed onto a substrate, and the system's electrical impedance is followed with time. The impedance is a measure of changes in the electrical conductivity of the cell layer. Typically, a small constant voltage at a fixed frequency or varied frequencies is applied to the electrode or electrode array, and the electrical current through the circuit is monitored over time. The ligand-induced change in electrical current provides a measure of cell response. The application of impedance measurements for whole cell sensing was demonstrated in 1984. Since then, impedance-based measurements have been applied to study a wide range of cellular events, including cell adhesion and spreading, cell micromotion, cell morphological changes, and cell death. Classical impedance systems suffer from high assay variability due to use of a small detection electrode and a large reference electrode. To overcome this variability, the latest generation of systems, such as CellKey system (MDS Sciex, South San Francisco, Calif.) and RT-CES (ACEA Biosciences Inc., San Diego, Calif.), utilize an integrated circuit having a microelectrode array.

Optical signals of GPCR activation with RWG biosensor—Cells are dynamic objects with relatively large dimensions, for example, tens of microns. RWG biosensors enable detection of ligand-induced changes within the bottom portion of cells, determined by the penetration depth of the evanescent wave. Furthermore, the spatial resolution of an optical biosensor is determined by the spot size (about 100 microns) of the incident light source. Thus, a highly confluent cell layer is generally used in order to achieve optimal assay results; and the sensor configuration can be viewed as a three-layer waveguide composite, consisting of a substrate, waveguide thin film, and a cell layer. Following a 3-layer waveguide biosensor theory in combination with cellular biophysics, for whole-cell sensing having a ligand-induced change in effective refractive index, the detected signal ΔN, is governed by equation (1):

$$\Delta N = S(N)\Delta n_C \qquad (1)$$
$$= S(N)\alpha d \sum_i \Delta C_i \left[ e^{\frac{-z_i}{\Delta Z_C}} - e^{\frac{-z_{i+1}}{\Delta Z_C}} \right]$$

where S(C) is the system sensitivity to the cell layer, and $\Delta n_c$ is the ligand-induced change in local refractive index of the cell layer sensed by the biosensor. $\Delta Z_c$ is the penetration depth into the cell layer, α is the specific refractive index increment (about 0.18/mL/g for proteins), $z_i$ is the distance where the mass redistribution occurs, and d is an imaginary thickness of a slice within the cell layer. Here the cell layer is divided into an equal-spaced slice in the vertical direction. It is assumed that the detected signal is, to a first order, directly proportional to the change in refractive index of the bottom portion of cell layer $\Delta n_c$. The $\Delta n_c$ is directly proportional to changes in local concentration of cellular targets or molecular assemblies within the sensing volume, given that the refractive index of a given volume within cells is largely determined by the concentrations of bio-molecules, mainly proteins. A weighted factor $\exp(-z_i/\Delta Z_c)$ is taken into account for a change in local protein concentration occurring, considering the exponentially decaying nature of the evanescent wave. Thus, the detected signal is a sum of mass redistribution occurring at distinct distances away from the sensor surface, each with unequal contribution to the overall response. Eq. 1 suggests that the detected signal with an RWG biosensor is sensitive primarily to the vertical mass redistribution, as a result of any change in local protein concentration and where and when it occurs. The detected signal is often referred to as a dynamic mass redistribution (DMR) signal.

Figure 6:
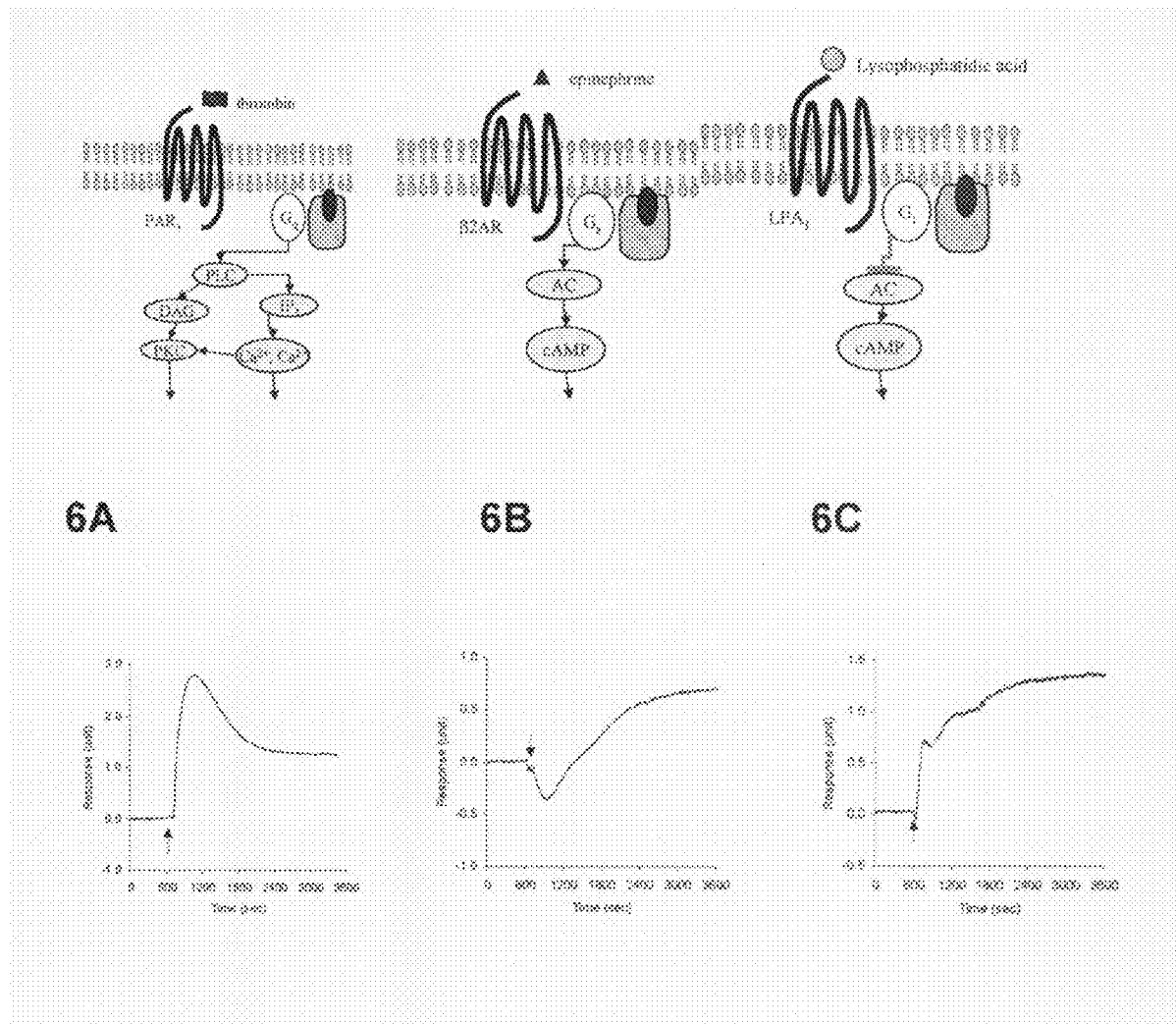
FIG. 6A and 6B illustrate GPCR signaling ($G_q$-, $G_s$-, and $G_i$-) of three major DMR signal class in live-cells using RWG biosensor, in embodiments of the disclosure.

GPCR activation leads to a series of spatial and temporal events, including ligand binding, receptor activation, protein recruitment, receptor internalization and recycling, second messenger alternation, cytoskeletal remodeling, gene expression, and cell adhesion changes, and like events. Each cellular event has its own characteristics regarding its kinetics, duration, amplitude, and mass movement. Thus it is reasonably assumed that these cellular events may contribute differently to the overall DMR signal, depending on the location where they occur. Using a panel of agonists targeting a variety of GPCRs, three classes of DMR signals were identified in human epidermoid carcinoma A431 cell, which reflect the signaling pathways mediated (Fang, Y., et al., "Non-invasive optical biosensor for assaying endogenous G protein-coupled receptors in adherent cells," *J. Pharmacol. Toxicol. Methods*, 2007, 55, 314-322) (see FIG. 6). Since each is correlated with the activation of a class of GPCRs depending on the G protein with which the receptor is coupled, the DMR signals obtained were named $G_q$-, $G_s$- and $G_i$-DMR signals, respectively. Each class of DMR signals exhibits distinct kinetic and dynamic characteristics that reflect the unique signaling integration mediated through different classes of GPCRs. Interestingly, the $G_q$-type DMR signal appears to be rapid, whereas the $G_s$-type DMR signal is comparatively slow. The unique characteristics of the DMR signals can be used to identify the G-protein coupling mechanism of orphan GPCRs as disclosed herein.

However, both the $G_q$ and $G_s$-DMR signals were found to be quite universal if not ubiquitous across multiple cell lines tested, while the $G_i$-DMR signals exhibit strong dependence on the cellular context as well as the receptors. Furthermore, for the same class of DMR signals mediated through the activation of different receptors in the same cell line or the activation of the same receptor in different cell lines, there are often significant differences in fine features such as the amplitudes and kinetics, reflecting the important role of cellular contexts in GPCR signaling as well as the unique signaling of each receptor. Thus, it is often difficult to assign a specific signaling pathway to a GPCR ligand-induced optical response solely based on its dynamics and shape. Pathway deconvolution is often required to determine the primary signaling pathway(s) that is(are) activated by a GPCR ligand and dominate the ligand-induced optical response.

Bioimpedance signals of GPCR activation—In a typical impedance-based cell assay, cells are brought into contact with a gold electrode arrayed on the bottom of culture wells. The total impedance of the sensor system is determined primarily by the ion environment surrounding the biosensor. Under application of an electrical field, the ions undergo field-directed movement and concentration gradient-driven diffusion. For whole-cell sensing, the total electrical impedance has four components: the resistance of the electrolyte solution, the impedance of the cell, the impedance at the electrode/solution interface, and the impedance at the electrode/cell interface. In addition, the impedance of a cell comprises two components: the resistance; and the reactance. The conductive characteristics of cellular ionic strength provide the resistive component, whereas the cell membranes, acting as imperfect capacitors, contribute a frequency-dependent reactive component. Thus, the total impedance is a function of many factors, including, for example, cell viability, cell confluency, cell numbers, cell morphology, degree of cell adhesion, ionic environment, the water content within the cells, and the detection frequency.

In the RT-CES system, a percentage of a small voltage applied is coupled into the cell interior. Such signals applied to cells are believed to be much smaller than the resting membrane potential of a typical mammalian cell and thus present minimal or no disturbance to cell function. The RT-CES system measures these changes in impedance and displays it as a parameter called the cell index. The cell index is calculated according to the equation (2):

$$CI = \max_{i=1,\ldots,N} \left( \frac{R_{cell}(f_i)}{R_0(f_i)} - 1 \right) \qquad (2)$$

where N is the number of frequency points at which the impedance is measured (e.g., N=3 for 10 kHz, 25 kHz, and 50 kHz), and $R_0(f)$ and $R_{cell}(f)$ are the frequency electrode resistance without cells or with cells present in the wells, respectively.

In the CellKey system, a change in sensor system's impedance is attributed to a change in complex impedance (delta Z or dZ) of a cell layer that occurs in response to receptor stimulation. At low frequencies, the small voltage applied induces extracellular currents (iec) that pass around individual cells in the layer. However, the conduction currents through cell membrane due to ion channels may also be important at low measurement frequencies. At high frequencies, they induce transcellular currents (itc) that penetrate the cellular membrane. The ratio of the applied voltage to the measured current for each well is its impedance (Z) as described by Ohm's law.

When cells are exposed to a stimulus, such as a receptor ligand, signal transduction events are activated that lead to complex cellular events such as modulation of the actin cytoskeleton that cause changes in cell adherence, cell shape and volume, and cell-to-cell interaction. These cellular changes individually or collectively affect the flow of extracellular and transcellular current, and therefore, affect the magnitude and characteristics of the measured impedance. Three types of impedance signals mediated through the activation of three classes of GPCRs are known (Leung, G., et al., *J. Assoc. Lab. Automat.*, 2005, 10, 258). Although not limited by theory, it is believed that these impedance signals are due to the different effects on the actin cytoskeleton that affect the cellular parameters measured by impedance, in response to the activation of different classes of GPCRs. It has been shown that activation of $G_q$ and $G_i$ GPCRs leads to increased actin polymerization, while stimulation of $G_s$ GPCRs leads to actin depolymerization.

2. GPCR Signaling and Signaling Integration

A characteristic common to living organisms is their dynamic ability to constantly coordinate the organism's activities with environmental changes. The function of communicating with the environment is achieved through a number of pathways that receive and process signals, such as from the external environment and also from different regions within the cell. Individual pathways transmit signals along linear tracts resulting in regulation of discrete cell functions. This type of information transfer is an important part of the cellular repertoire of regulatory mechanisms. However, as increasingly larger numbers of cell signaling components and pathways are identified and studied, it has become apparent that these linear pathways are not free-standing entities but parts of larger networks.

One of the more surprising results from the initial studies of networks and component interactions in different cell types is that there may be a general signaling network that receives signals from cell type-specific inputs (i.e., receptors), and engage cell type-specific machinery. The molecular identity of the signaling components and their interacting partners may be cell type-specific, but the overall function of these components and the logic of the chemical signaling circuitry is preserved from cell-type to cell-type.

Although not limited by theory, it is believed that networks can result from interconnections between signaling pathways. Such interconnections can occur because the same signaling component is capable of receiving signals from multiple inputs. Such networking may occur within similar classes of signaling pathways, such as between the Ras and Rho pathways, or between different pathways, such as the $G_{s\alpha}$/cAMP and MAP kinase pathways.

GPCR Signaling

GPCRs constitute a superfamily of seven transmembrane spanning proteins that respond to a diverse array of sensory and chemical stimuli, such as light, odor, taste, pheromones, hormones, and neurotransmitters. GPCRs transduce the information provided by these stimuli into intracellular second messengers that are interpreted as meaningful signals by the cell. This process involves the coupling of agonist-activated GPCRs to a wide variety of effector systems via their interaction with heterotrimeric guanine nucleotide binding proteins (G proteins). The binding of agonist to a GPCR selects for a receptor conformation state that promotes the exchange of GDP for GTP on the G protein-subunit and is presumed to allow the dissociation of the G protein G- and G-subunits. Subsequently, the activated G- and G-subunits positively, negatively, or both, regulate the activity of effector enzymes and ion channels. Agonist activation of a GPCR results in the G protein-dependent activation of effector systems, and also sets in place a series of molecular interactions that allows for: 1) feedback regulation of G protein coupling, 2) receptor endocytosis, and 3) signaling through G protein-independent signal transduction pathways.

In addition to signaling via heterotrimeric G proteins, it is now recognized that GPCRs act as scaffolds promoting the formation and compartmentalization of G protein-independent signal transduction complexes. A growing number of proteins have been identified that bind GPCRs and either couple GPCRs to G protein-independent signal transduction pathways or alter G protein specificity and agonist selectivity. The list of GPCR interacting proteins now includes, for example: GRKs, arrestins, calmodulin, calcyon, A kinase-anchoring protein (AKAP), tubulin, receptor activity modulating proteins Janus kinase 2, PDZ domain-containing proteins (e.g., NHERF, RGS12), SH3 domain-containing adaptor molecules (e.g., Grb2, Nck, c-Src, and endophilin), and small G proteins, and like proteins.

GPCRs can be classified into at least four major categories, depending on G proteins with which the receptor is coupled including $G_q$-coupled receptors that lead to $Ca^{2+}$ mobilization, $G_{i/o}$-coupled receptors that lead to decreased cAMP, $G_s$-coupled receptors that cause cAMP accumulation, and $G_{12/13}$-coupled receptors that activate small GTPases such as Rho.

GPCR Signaling and Integration at Intracellular cAMP Level

Adenylyl cyclases (ACs) have been viewed as a junction or signal integrator in cell signaling networks. Distinct adenylyl cyclase isoforms have different signal receiving capabilities. All adenylyl cyclase isoforms are capable of producing cAMP in response to signals from $G_s$-coupled receptors. However, these isoforms are distinct in their ability to receive signals from a wide variety of inputs. cAMP levels in the cell could serve as an indicator of the balance of signals between many pathways. This complex situation detailing the signal-receiving capabilities of adenylyl cyclases is depicted in FIG. 1. Referring to the Figures, FIG. 1 is a schematic illustrating adenylate cyclase isoform-dependent cell signaling pathways. Adenylate cyclases are targets of multiple regulatory signaling pathways and can respond differently depending upon which cyclase group they belong to.

In cells, there are nine AC isoforms—all activated by $G_{s\alpha}$, with some, but not all, being inhibited by $G_{i/o\alpha}$ subunits. To a greater or lesser extent, each of AC isoforms receives inputs from more than one signaling pathway, so that cellular responses are tuned by the isozymes they express. An example is that while $Ca^{2+}$/CaMII (calmodulin-dependent protein kinase II) activate ACI (adenylate cyclase subtype 1), $Ca^{2+}$ inhibits ACV (adenylate cyclase subtype 5) and ACVI (AC subtype 6). Another example is that while ACV and ACVI are inhibited by $G_{i\alpha}$, ACII (AC subtype 2) and ACIV (AC subtype 4) appear to be unresponsive to $G_{i\alpha}$.

Cellular cAMP responses also depend on the G protein selectivity/specificity of the receptors being stimulated. $Ca^{2+}$ affects different adenylyl cyclase in opposite ways. ACI is stimulated by $Ca^{2+}$/CaMII, ACV and ACVI are inhibited by $Ca^{2+}$ and various forms of phosphorylation by PKC (protein kinase C) and PKA, and ACs of the ACII, IV and VII appear insensitive to changes in intracellular $Ca^{2+}$. In the intact cell, the effects of $Ca^{2+}$ depend not only on the isozyme that is expressed but also on the site at which $Ca^{2+}$ increases take place. In cells expressing ACII, ACIV or ACVII, increases in Ca$^{2+}$ and diacylglycerol (DAG) may lead to an increase in cAMP mediated by Ca$^{2+}$ and DAG stimulated phosphorylation of the cAMP forming enzymes. In contrast, PKA-mediated phosphorylation may act as a negative feedback regulator of ACV and ACVI.

The nine membrane-bound isoforms of the enzyme adenylate cyclase are highly regulated by neurotransmitters and drugs acting through G protein-coupled receptors to modulate intracellular cAMP levels. In general, acute activation of G$_s$-coupled receptors stimulates cAMP accumulation, whereas acute activation of G$_{i/o}$-coupled receptors typically inhibits cAMP accumulation. It is also well established that persistent activation of G-protein coupled receptors will alter subsequent drug-modulated cAMP accumulation. These alterations are believed to represent cellular adaptive responses following prolonged receptor activation.

Heterologous Sensitization. One phenomenon commonly observed, heterologous sensitization of adenylate cyclase, is characterized by an enhanced responsiveness to drug-stimulated cAMP accumulation following persistent activation of G$_{i/o}$-coupled receptors. Heterologous sensitization of adenylate cyclase was originally proposed to explain tolerance and withdrawal following chronic opiate administration and may be a mechanism by which cells adapt to prolonged activation of inhibitory receptors. Such an adaptive mechanism has been suggested to play a role in, for example, the processes of drug addiction and withdrawal from drug abuse, and in psychiatric disorders including schizophrenia and depression. Heterologous sensitization may also involve the simultaneous activation of multiple G$_{i/o}$ proteins. For example, the magnitude of selective G$_o$-induced heterologous sensitization seems to be reduced when compared with sensitization in cells where the entire endogenous G$_{i/O}$ pool was available.

Heterologous Desensitization. Desensitization of receptor-mediated cellular responses is a complex process which can involve multiple pathways including: a) receptor uncoupling from G protein, b) sequestration of receptors away from the plasma membrane, and c) down-regulation of signaling proteins. Receptor desensitization is commonly homologous (that is which is agonist specific and dependent on receptor occupancy). In contrast, the direct activation of adenylate cyclases by their activators or PKA by cell permeable cAMP can lead to receptor phosphorylation, which is most often associated with heterologous desensitization (that is which is agonist non-specific and therefore not dependent on receptor occupancy).

GPCR Signaling and Integration at Intracellular Ca$^{2+}$ Level

Similarly, intracellular Ca$^{2+}$ level also plays important role in GPCR signaling. The intracellular Ca$^{2+}$ level is commonly regulated by ion channels. Multiple G protein-mediated pathways are known to converge to modulate calcium channels. The complex timing of events is controlled by interactions between components of several signaling pathways and a dynamic network of cytoskeletal and scaffold structures that can serve as the stratum for interaction between these components and the calcium channel. Many of the receptors known to induce modulation of calcium channels are coupled to heterotrimeric G$_{i/o}$ proteins, as shown by the observation that pretreatment of cells with pertussis toxin (PTX) abolishes inhibition of calcium channels. Inhibition of calcium channels can occur through membrane-delimited or second messenger-mediated signals. The membrane-delimited pathway is mediated by the direct binding of G protein βγ-subunits (G$_{βγ}$) and results in voltage-dependent inhibition of Cav2.2 channels.

Pathway De-Convolution Using Label-Free Biosensor Assays

GPCR signaling is sophisticated and highly complex—a receptor can mediate signaling through G protein-dependent and independent pathways; and a receptor can mediate through multiple G protein-dependent pathways. Since label-free biosensor cell assays measure an integrated cellular response (e.g., DMR signal with optical biosensor, or bio-impedance with electronic biosensor), the activation of a receptor may lead to an atypical biosensor response or output signal, depending, for example, on the nature of the ligand(s) and the cellular contexts (or backgrounds). For example, two endogenous G$_i$-coupled receptors, LPA receptors (FIG. 6C) and nicotinic acid receptors (FIG. 5A), lead to two different types of DMR signals in the same A431 cellular line, reflecting the complexity and uniqueness of each receptor-induced signaling process. Furthermore, the same LPA receptors in A431 cells could lead to different types of DMR signals, dependent on the cellular status, such as fully quiescent states versus proliferating states (FIG. 6C; data not shown). Thus, although label-free biosensor assays follow the receptor signaling in real time and provide well-defined kinetics response, the dynamics of the kinetic response alone may not be a predictive indicator for pathway assignment.

By taking advantage of how cells integrate GPCR signaling, at least two different methods can be used to de-convolute GPCR signaling using label-free biosensor assays. A first method (Method 1) elevates intracellular cAMP level using an AC activator such as forskolin or NKH 447, or a PKA activator such as a cell preamble cAMP analog. Based on the differential impact or effect of the elevated cAMP level on the GPCR ligand-induced biosensor's output, one can de-convolute GPCR signaling. The elevated intracellular cAMP level has little or no inhibition effect on G$_q$ or G$_{12/13}$ signaling, completely attenuates G$_s$ signaling through the heterologous desensitization, and enhances G$_i$ signaling at their EC$_{50}$ concentrations through heterologous sensitization.

A second method (Method 2) suppresses the activity of intracellular phospholipase C (PLC) activity using either a PLC inhibitor such as U73122, or a PLC gene suppressor interference RNA. Such approach provides a complementary approach to de-convolute GPCR signaling using label-free assays. The suppression of PLC activity has little effect on G$_s$ or G$_{12/13}$ signaling, but completely attenuates G$_q$ signaling, and partially attenuates G$_i$ signaling. The two approaches can be used independently, or in combination to de-convolute GPCR signaling using label-free cell assays. The above two methods and their respective effects on the indicated GPCR are summarized in the accompanying table.

| GPCR | Method 1 | Method 2 |
| --- | --- | --- |
| G$_q$ | slight/partial inhibition | complete inhibition |
| G$_i$ | enhanced (hetero-sensitization) | slight/partial inhibition |
| G$_s$ | complete attenuation (hetero-desensitization) | little/no inhibition |
| G$_{12/13}$ | little/no inhibition | little/no inhibition |

EXAMPLES

The following examples serve to more fully describe the manner of using the above-described disclosure, and to further set forth the best modes contemplated for carrying out various aspects of the disclosure. It is understood that these examples do not limit the scope of this disclosure, but rather are presented for illustrative and demonstrative purposes.

Biosensor-based live-cell assays allow detection of cellular responses resulting from activation of adenylate cyclase by, for example, forskolin, followed by activation of a G protein-coupled receptor, and vice versa. The persistent activation of adenylate cyclase by forskolin can sensitize or desensitize a G protein-coupled receptor to agonist stimulation, depending on the receptor type.

Experimental Procedures

Materials—Forskolin and epinephrine were obtained from Tocris (St. Louis, MO). Histamine and nicotinic acid were obtained from Sigma Chemical Co. (St. Louis, MO). EPIC®384-well cell assay microplates were obtained from Corning Inc (Corning, NY). The microplates, in which each well consists of a resonant waveguide grating (RWG) biosensor, are ready-to-culture and were used directly without any pretreatments.

Cell culture—Human epidermoid carcinoma A431 cells (American Type Cell Culture) were grown in Dulbecco's modified Eagle's medium (DMEM) supplemented with 10% fetal bovine serum (FBS), 4.5 g/liter glucose, 2 mM glutamine, and antibiotics. About $1.8 \times 10^4$ cells at passage 3 to 8 suspended in 50 µL of the DMEM medium containing 10% FBS were placed in each well of a 384-well microplate, and were cultured at 37° C. under air/5% $CO_2$ for about 1 day, followed by about 20 hr starvation through continuously culturing in the serum-free DMEM.

Optical biosensor system and cell assays—CORNING® EPIC® wavelength interrogation system was used. The system is stand-alone and consists of a temperature-control unit, an optical detection unit, and an on-board liquid handling unit with robotics. The temperature-control unit is built-in to minimize temperature fluctuation, if any. Inside this unit, there are two side-by-side stacks for holding both the sensor microplates and compound source plates. Once stable temperature is reached (typically within 1 hr), a sensor microplate is transferred by the robotics into the plate holder directly above the detection system, while a source plate is moved to an appropriate compartment so that it is readily addressable by the on-board liquid handling unit.

The detection unit is centered on integrated fiber optics to measure, for example, the wavelength shift of the resonant lights due to ligand-induced dynamic mass redistribution in living cells. A broadband white light source centered on 830 nm, generated through a fiber optic and a collimating lens at nominally normal incidence through the bottom of the microplate, was used to illuminate a small region of the grating surface. A detection fiber for recording the reflected light was bundled with the illumination fiber. A series of illumination/detection heads were arranged in a linear fashion, so that reflection spectra are collected from the 16-wells within the same column of a 384-well microplate at once. The whole plate was scanned by the illumination/detection heads so that each sensor can be addressed multiple times, and each column was addressed in sequence, leading to a kinetic measurement of cellular responses with a time interval of 6 or 13 seconds.

For kinetic assays, the cells were washed with HBSS (Hanks Balanced Salt Solution with 20 mM HEPES) buffer. After 1 hour incubation within the detection system, the sensor plate was scanned and a baseline response was recorded. Then, compound solutions were transferred into the sensor plate using the on-board liquid handling system, and the cell responses were then recorded for another period of time. Similarly, a second optional step that includes, for example, adding a different compound solution can be accomplished to determine the impact of the first compound on the second ligand-induced response. The lid of the sensor microplates was on throughout the assay, except for a short period of time (about 1 min.) when the compounds were introduced. The plate lid was handled automatically by the robotics. All assay measurements were carried out at controlled temperature (28° C.).

Statistical analysis—Unless specifically mentioned, three replicates were carried out for each measurement or each compound. The standard deviation was derived from these measurements (n=3). The assay coefficient of variation was found to be typically less than about 10%. All dose-dependent responses were analyzed using non-linear regression method with Prism software (available from Graph Pad).

Results and Discussions

Figure 2:
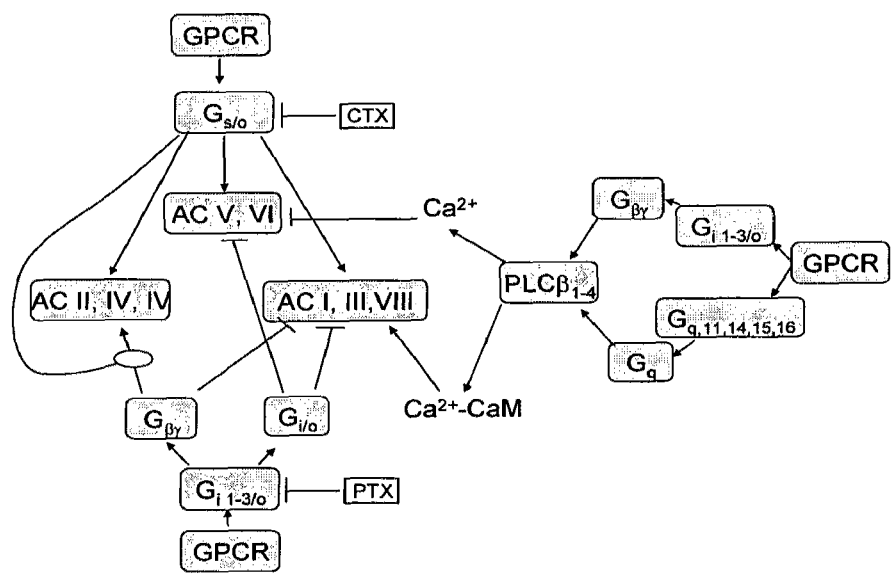
FIG. 2 is a schematic illustrating cross-talk from the $G_q$ ($G_{\alpha q}$), $G_i$ ($G_{\alpha i}$) and $G_{s/o}$ ($G_{\alpha s/o}$) and $G_{\beta\gamma}$ mediated signaling pathways to the intracellular adenylate cyclase and its impact on cAMP levels, in embodiments of the disclosure.

FIG. 2 is a schematic illustrating cross-talk from the $G_q$ ($G_{\alpha q}$), $G_i$ ($G_{\alpha i}$) and $G_{s/o}$ ($G_{\alpha s/o}$) and $G_{\beta \gamma}$ mediated signaling pathways to the intracellular adenylate cyclase, which may generate an increase or a decrease in cAMP levels depending upon the subset of adenylate cyclases expressed in the target cell.

Figure 3:
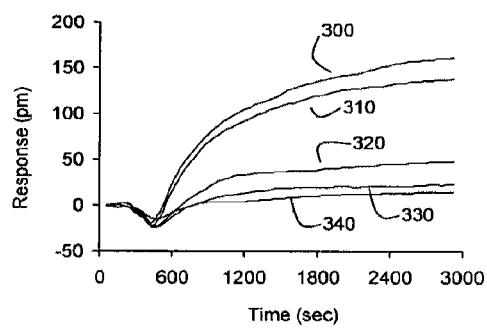
FIGS. 3A and 3B illustrate, respectively, the effects of forskolin pretreatment on the NECA-induced $G_s$ response; and the effects of N-ethyladenosine-5'-uronic acid (NECA) pretreatment on forskolin-induced $G_s$ responses in quiescent A431 cells, in embodiments of the disclosure.
Figure 3:
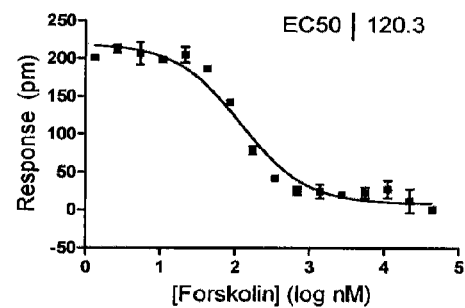
Figure 3:
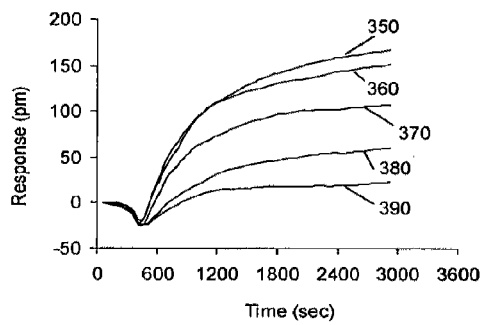
Figure 3:
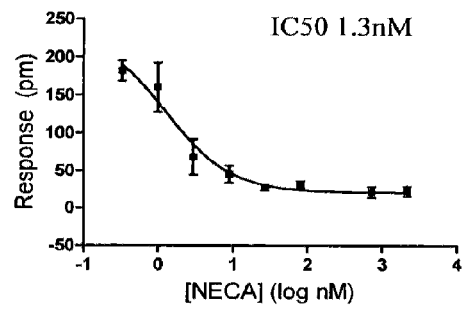

FIG. 3A shows in embodiments an example of the optical response resulting from forskolin pretreatment, followed by activation of a $G_s$-coupled receptor (A2 adenosine receptor) in quiescent A431 cells. Although the activation of adenylate cyclase by forskolin typically acts synergistically with the activation of a $G_s$-coupled receptor, pretreatment of A431 cells with various concentrations of forskolin for 1 h, followed by exposure to 100 nM NECA (N-ethyladenosine-5'-uronic acid; an A2-specific agonist) leads to heterologous desensitization, i.e., a decrease in responsiveness of the A2 receptor to stimulation by its agonist. Similarly, pretreatment of A431 cells with various concentrations of NECA for 1 h desensitizes adenylate cyclase and attenuates the forskolin-induced responses (FIG. 3B). The observation of heterologous desensitization suggests that cross-talk occurs between the signaling pathways resulting from activation of adenylate cyclase and activation of the A2 receptor. Although not limited by theory a possible mechanism of cross-talk between these two pathways is that upon activation of adenylate cyclase by forskolin, cAMP is produced and activates PKA. PKA in turn may phosphorylate the $G_s$ receptors, and cause complete inhibition of the $G_s$-mediated response. Accordingly, FIGS. 3A and 3B, respectively, illustrate: 3A) forskolin pretreatment on the NECA-induced $G_s$ response; and 3B) of the effects NECA pretreatment on forskolin-induced responses in quiescent A431 cells. Pretreatment of A431 cells with various concentrations of forskolin (300=5 nM, 310=44 nM, 320=174 nM, 330=348 nM, 340=690 nM), followed by exposure to 100 nM NECA, lead to an attenuation of the NECA-induced responses. The inhibitory effect by forskolin is believed to be due to cross-talk between signaling pathways resulting from activation of adenylate cyclase by forskolin and activation of A2 adenosine receptors by NECA. Similarly, pretreatment of A431 cells with various concentrations of NECA (350=3 nM, 360=384 nM, 370=696 nM, 380=5 nM, 390=11 nM), followed by 1 µM forskolin, showed the A2 receptor agonist inhibiting forskolin binding with an $IC_{50}$ of 1.3 nM.

Figure 4:
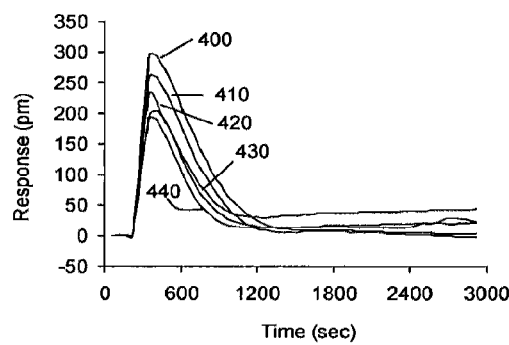
FIGS. 4A and 4B illustrate, respectively, the effects of forskolin pretreatment on histamine-induced $G_q$ response; and the effects of histamine pretreatment on forskolin-induced $G_q$ responses in quiescent A431 cells, in embodiments of the disclosure.
Figure 4:
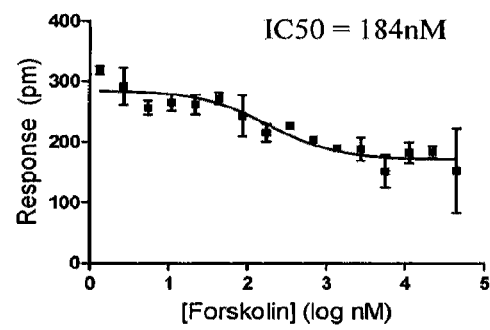
Figure 4:
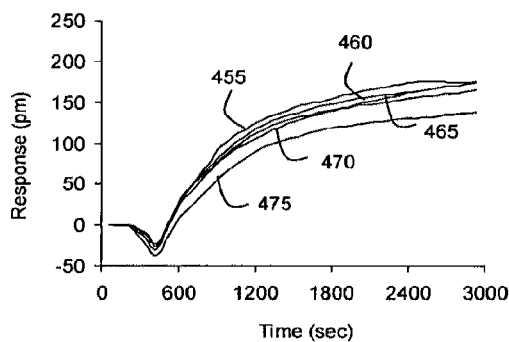
Figure 4:
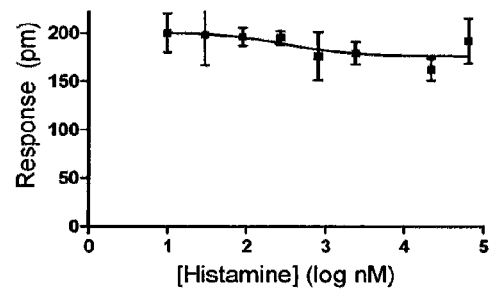

FIG. 4A shows an example of the optical response resulting from forskolin pretreatment, followed by activation of a $G_q$-coupled receptor (H1 histamine receptor) in quiescent A431 cells. Pretreatment of A431 cells with various concentrations of forskolin for 1 h, followed by exposure to 100 nM histamine (an H1-specific agonist) also leads to partial desensitization. The dose-dependent partial inhibition by forskolin pretreatment led to an $IC_{50}$ of about 184 nM, corresponding to the potency of forskolin. The observation of agonist-induced desensitization in this case again suggests that some cross-talk at specific isoforms of adenylate cyclases occurs between the signaling pathways resulting from activation of all endogenous adenylate cyclases by forskolin and from activation of the H1 receptor. FIGS. 4A and 4B illustrate, respectively: 4A) the effects of forskolin pretreatment on histamine-induced $G_q$ response; and 4B) of histamine pretreatment on forskolin-induced responses in quiescent A431 cells. Pretreatment of A431 cells with various concentrations of forskolin (400=3 nM, 410=5 nM, 420=174 nM, 430=696 nM, 440=2,784 nM), followed by exposure to 100 nM histamine, lead to an attenuation of the histamine-induced responses. The inhibitory effect by forskolin is believed to be due to cross-talk between signaling pathways resulting from activation of adenylate cyclase by forskolin and activation of H1 histamine receptors by histamine. Similarly, pretreatment of A431 cells with various concentrations of histamine (455=30 nM, 460=90 nM, 465=9.9 nM, 470=270 nM, 475=810 nM), followed by 1 µM forskolin, showed the H1 receptor agonist slightly inhibiting the forskolin response with an $IC_{50}$ of 301 nM.

Figure 5:
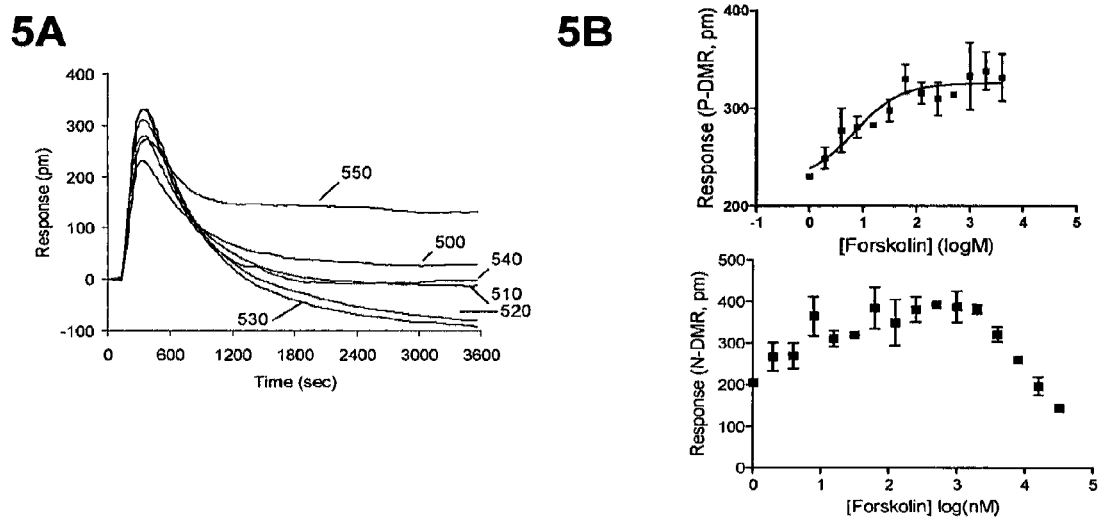
FIG. 5A and 5B illustrate the effect of forskolin pretreatment on nicotinic acid-induced $G_i$ responses in quiescent A431 cells, in embodiments of the disclosure.

FIG. 5 shows an example of the cellular response resulting from forskolin pretreatment, followed by activation of a $G_i$-coupled receptor (nicotinic acid receptor HM74 receptor) in quiescent A431 cells. In contrast to the activation of $G_s$-and $G_q$-coupled receptors, pretreatment of A431 cells with various concentrations of forskolin for 1 h, followed by exposure to 25 µM nicotinic acid (an HM74-specific agonist) leads to potentiation of the H1-induced response, reaching a maximum value at the $EC_{50}$ of forskolin. FIG. 5A illustrates the effect of forskolin pretreatment on nicotinic-induced $G_i$ responses in quiescent A431 cells. Pretreatment of A431 cells with various concentrations of forskolin (i.e., 500=0 nM, 510=4 nM, 520=32 nM, 530=125 nM, 540=4,000 nM, 550=32,000 nM), followed by 25 µM nicotinic acid, leads to potentiation of the nicotinic acid-induced responses. The potentiation of the $G_i$ response is believed to be due to heterologous sensitization.

FIGS. 6A to 6C respectively show GPCR signaling ($G_q$-, $G_s$-, and $G_i$-) of three major classes of DMR signals in live-cells using RWG biosensor: 6A) $G_q$-signaling and its DMR signal (protease activated receptor subtype 1 in Chinese hamster ovary cells, 10 unit/mL thrombin); 6B) $G_s$-signaling and its DMR signal ($\beta_2$-adrenergic receptors in A431 cells, 2 nM epinephrine); and 6C) $G_i$-signaling and its DMR signal (lysophophatidic acid (LPA) receptor subtype 1 in A431, 100 nM LPA). The broken arrows indicate the time when an agonist solution was introduced.

Figure 7:
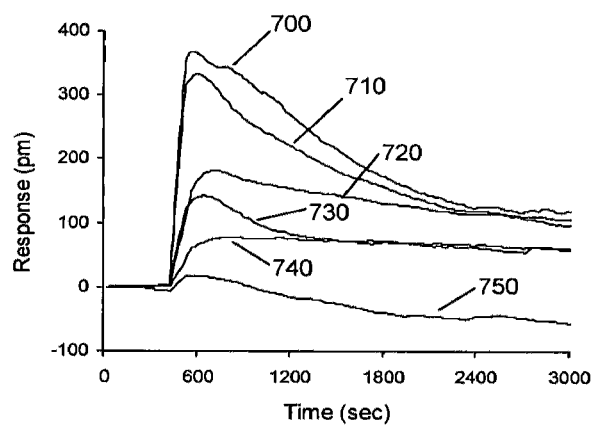
FIGS. 7A and 7B show, respectively, the effect of U73122 pretreatment on histamine-induced DMR signal, and its P-DMR amplitude, in quiescent A431 cells, in embodiments of the disclosure.
Figure 7:
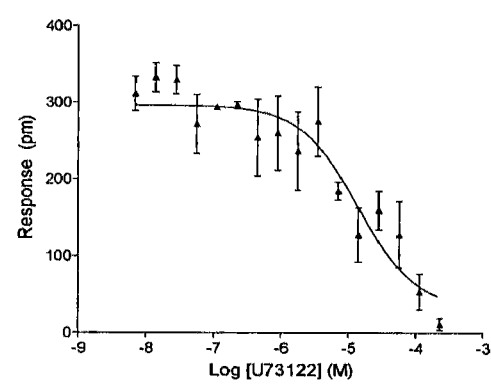

FIG. 7A shows the effect of U73122 pretreatment on histamine-induced DMR signals in quiescent A431 cells. The pretreatment of A431 cells with various concentrations of U73122 (i.e., 700=0 µM; 710=1.78 µM; 720=7.15 µM; 730=28.5 µM; 740=114 µM; 750=228 µM), followed by stimulation with 1,000 nM histamine, leads to dose-dependent inhibition of the histamine-induced DMR response. Histamine is a natural agonist for endogenously expressed $G_q$-coupled receptor histamine receptor subtype 1 in A431 cells. Based on the P-DMR amplitude of the histamine response shown in FIG. 7B, U73122 at high doses can completely inhibit the histamine response.

The disclosure has been described with reference to various specific embodiments and techniques. However, it should be understood that many variations and modifications are possible while remaining within the spirit and scope of the disclosure.

References

1. Y, Fang et al., "Label-Free Biosensors and Cells", PCT App. No. PCT/US2006/013539 (Pub. No. WO 2006/108183).
2. Fang, Y., et al., "Resonant waveguide grating biosensor for living cell sensing," *Biophys. J.*, (2006) 91, 1925-1940.

What is claimed is:

1. A label-free method for GPCR signaling pathway determination, the method comprising:
    immobilizing live cells on a resonant waveguide grating (RWG) biosensor;
    contacting the immobilized live cells with a substance that elevates intracellular cAMP and activates protein kinase A in the live cells;
    contacting the substance-contacted live cells with a GPCR ligand;
    detecting and comparing the GPCR ligand-induced biosensor response of the live cells in the presence and absence of the substance; and
    determining the signalling pathways of the GPCR activated by the ligand, wherein the substance-induced inhibition of the GPCR ligand-induced response indicates that the GPCR signals via $G_{\alpha s}$ pathway, the substance-induced partial suppression of the GPCR ligand-induced response indicates that the GPCR signals via a $G_{\alpha q}$ pathway, and the substance-induced potentiation of the GPCR ligand-induced response indicates that the GPCR signals via a $G_{\alpha i}$ pathway, wherein the response is a dynamic mass redistribution (DMR) signal measured by the resonant waveguide biosensor, and the substance is a probe molecule to differentiate all classes of signalling mediated through the GPCR.

2. The method of claim 1 wherein the substance comprises an adenylate activator.

3. The method of claim 2 wherein the adenylate activator comprises at least one of forskolin, NKH477, 1,9-dideoxy-forskolin, 7-deacetyl-7-O-hemisuccinyl-forskolin, or combinations thereof.

4. The method of claim 1 wherein the substance comprises a cell-permeable cAMP analog.

5. The method of claim 4 wherein the cell-permeable cAMP analog comprises at least one of (S)-adenosine, cyclic 3',5'-(hydrogenphosphorothioate)triethyl ammonium, 8-bromoadenosine- 3',5'-cyclic monophosphate, 8-chloroadenosine- 3',5'-cyclic monophosphate, N6, 2'-O-dibutyryladenosine-3', 5'-cyclic monophosphate, or a combination thereof.

6. The method of claim 1 wherein the GPCR ligand comprises at least one of an agonist, a partial agonist, or an inverse agonist that mediates signaling through a receptor expressed in the live cells.

7. The method of claim 1 wherein contacting the immobilized live cells with the substance first causes intracellular cAMP elevation and second causes protein kinase A activation.

8. The method of claim 1 wherein immobilizing live cells on a biosensor comprises incubating live-cells on a biosensor surface to a confluency of from about 1 percent to about 99 percent biosensor surface coverage.

9. The method of claim 1 wherein the elevated intracellular cAMP level has partial inhibition effect on $G_q$ or $G_{12/13}$ signaling, completely attenuates $G_s$ signaling through heterologous desensitization, enhances $G_i$ signaling induced by an agonist at its $EC_{50}$ concentrations for the receptor through heterologous sensitization, and permits de-convolution and determination of live cell GPCR signalling, wherein the $EC_{50}$ of the agonist for the receptor is determined via dose-dependent dynamic mass redistribution measurement with the label-free RWG biosensor.

10. The method of claim 1 further comprising combining a phospholipase C suppressor with the adenylate cyclase activator.

11. The method of claim 1 further comprising at least one of a pretreatment, an intermediate treatment, a post-treatment, or a combination thereof of the immobilized live cells with a stimulus.

12. The method of claim 1 wherein the alteration of the GPCR ligand-induced biosensor response induced by the substance is indicative of the signalling pathway being activated by the ligand, wherein the signalling pathway being activated is at least one of Gq, Gi, Gs, $G_{12/13}$, or a combination thereof.

13. The method of claim 1 wherein the alteration of the GPCR ligand-induced biosensor response by the substance differentiates among different classes of G protein signaling, differentiates between signaling of GPCRs and signaling of non-GPCRs, or both.

14. A method for GPCR signaling pathway determination, the method comprising:
    immobilizing live cells on a resonant waveguide grating (RWG) biosensor;
    contacting the immobilized live cells with a GPCR ligand;
    contacting the GPCR ligand-contacted live cells with a substance that elevates intracellular cAMP and activates protein kinase A in the live cells;
    detecting and comparing the substance-induced biosensor response of the live cells in the presence and absence of the GPCR ligand; and
    determining the signal pathway of the GPCR induced by the ligand, wherein the alteration of the substance-induced response by the ligand indicates the signalling pathway being activated by the ligand, the substance-induced response is a dynamic mass redistribution response, and the substance is a probe molecule to differentiate all classes of signalling mediated through the GPCR.

15. The method of claim 14 wherein the GPCR is the endogenous nicotinic acid receptor HM74a expressed in human epidermoid A431 cells.

16. The method of claim 14 wherein the GPCR ligand comprises at least one of an agonist, a partial agonist, an inverse agonist that mediates signaling through the GPCR expressed in the live-cells, or a combination thereof.

17. A method for GPCR signaling pathway determination, the method comprising:
    immobilizing live cells on a resonant waveguide grating (RWG) biosensor;
    contacting the immobilized live-cells with a substance that suppresses intracellular phospholipase C (PLC) activity in the live cells;
    contacting the PLC-suppressed live cells with a GPCR ligand;
    detecting and comparing the GPCR ligand-induced biosensor response of the live cells in the presence and absence of the substance; and
    determining the GPCR signal pathway of the receptor induced by the ligand, wherein the inhibition of the GPCR ligand-induced response indicates that the GPCR signals via $G_{\alpha q}$ pathway, the substance-induced partial suppression of the GPCR ligand-induced response indicates that the GPCR signals via a $G_{\alpha i}$ pathway, the substance-induced little change of the GPCR ligand-induced response indicates that the GPCR signals via a $G_{\alpha s}$ pathway, and the substance is a probe molecule to differentiate all classes of signalling mediated through the GPCR.

18. The method of claim 17 wherein the substance that suppresses intracellular phospholipase C (PLC) activity in the live-cells comprises a PLC inhibitor, a PLC gene suppressor interference RNA, or a combination thereof.

19. The method of claim 18 wherein the PLC inhibitor comprises U73122.

20. The method of claim 19 wherein the suppression of PLC activity has limited effect on $G_s$, or $G_{12/13}$ signaling, completely attenuates $G_q$ signaling, and partially attenuates $G_i$, signaling; and permits de-convolution and determination of live-cell GPCR signaling.

* * * * *